United States Patent
Yamazaki

(10) Patent No.: US 9,937,706 B2
(45) Date of Patent: Apr. 10, 2018

(54) DEVICE FOR INSPECTING PRINT MATERIAL, METHOD OF INSPECTING PRINT MATERIAL, AND PROGRAM

(71) Applicant: FUJIFILM Corporation, Tokyo (JP)

(72) Inventor: Yoshirou Yamazaki, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/423,443

(22) Filed: Feb. 2, 2017

(65) Prior Publication Data

US 2017/0144464 A1    May 25, 2017

Related U.S. Application Data

(63) Continuation of application No. PCT/JP2015/072790, filed on Aug. 11, 2015.

(30) Foreign Application Priority Data

Aug. 27, 2014 (JP) ................ 2014-172740

(51) Int. Cl.
*B41F 33/00* (2006.01)
*G01N 21/93* (2006.01)
(Continued)

(52) U.S. Cl.
CPC ......... *B41F 33/0036* (2013.01); *B41J 29/393* (2013.01); *G01N 21/93* (2013.01); *G07D 7/2075* (2013.01); *B65H 2511/52* (2013.01)

(58) Field of Classification Search
CPC ............. B41F 33/0036; G07D 7/2075; G06K 15/408; G06K 15/4065
See application file for complete search history.

(56) References Cited

U.S. PATENT DOCUMENTS 8,170,290 B2    5/2012 Rauh et al.
2007/0256586 A1*  11/2007 Bonikowski ........... B65H 39/00
                                                                101/484
(Continued)

FOREIGN PATENT DOCUMENTS

DE    10 2006 050 347 A1    4/2008
EP         2 484 523 A1    8/2012
(Continued)

OTHER PUBLICATIONS

International Search Report (ISR) (PCT Form PCT/ISA/210), in PCT/JP2015/072790, dated Oct. 20, 2015 and English translation thereof.
(Continued)

*Primary Examiner* — Shelby Fidler
(74) *Attorney, Agent, or Firm* — McGinn IP Law Group, PLLC

(57) ABSTRACT

This object is solved by a device for inspecting a print material, including evaluation value acquisition means for inspecting a plurality of print materials and acquiring an evaluation value indicating quality of each print material, allowed-number-of-failed-product acquisition means for acquiring an allowed number of failed products among the plurality of print materials, determination criterion determination means for determining a determination criterion in which the number of failed products is equal to or smaller than the allowed number of failed products and a sum of evaluation values of passed products becomes a highest-quality value, pass and fail determination means for determining pass or fail of each print material on the basis of the determination criterion and the evaluation value of each print material, and output means for outputting a determination result of the pass and fail determination means.

19 Claims, 5 Drawing Sheets

(51) Int. Cl.
    *G07D 7/20*      (2016.01)
    *B41J 29/393*    (2006.01)

(56)            References Cited

U.S. PATENT DOCUMENTS

2008/0101679 A1*    5/2008   Rauh .................. B41F 33/0036
                                                        382/137
2011/0304091 A1*   12/2011   Hirano .................... G06M 7/06
                                                        271/3.14
2011/0307095 A1*   12/2011   Chretinat ............. B41F 33/025
                                                        700/217
2012/0199025 A1     8/2012   Funada

FOREIGN PATENT DOCUMENTS

JP      H 06-246904 A      9/1994
JP      2005-205797 A      8/2005
JP      2005-271431 A      10/2005
JP      2007-024669 A      2/2007
JP      2009-133741 A      6/2009
JP      2012-161951 A      8/2012
JP      2012-232561 A      11/2012

OTHER PUBLICATIONS

Written Opinion of the ISA/JPO (PCT/ISA/237) in PCT/JP2015/072790 dated Oct. 20, 2015 and English translation thereof.
German Office Action dated Nov. 7, 2017 in corresponding Patent Application No. 11 2015 003 903.1 with an English translation thereof.

* cited by examiner

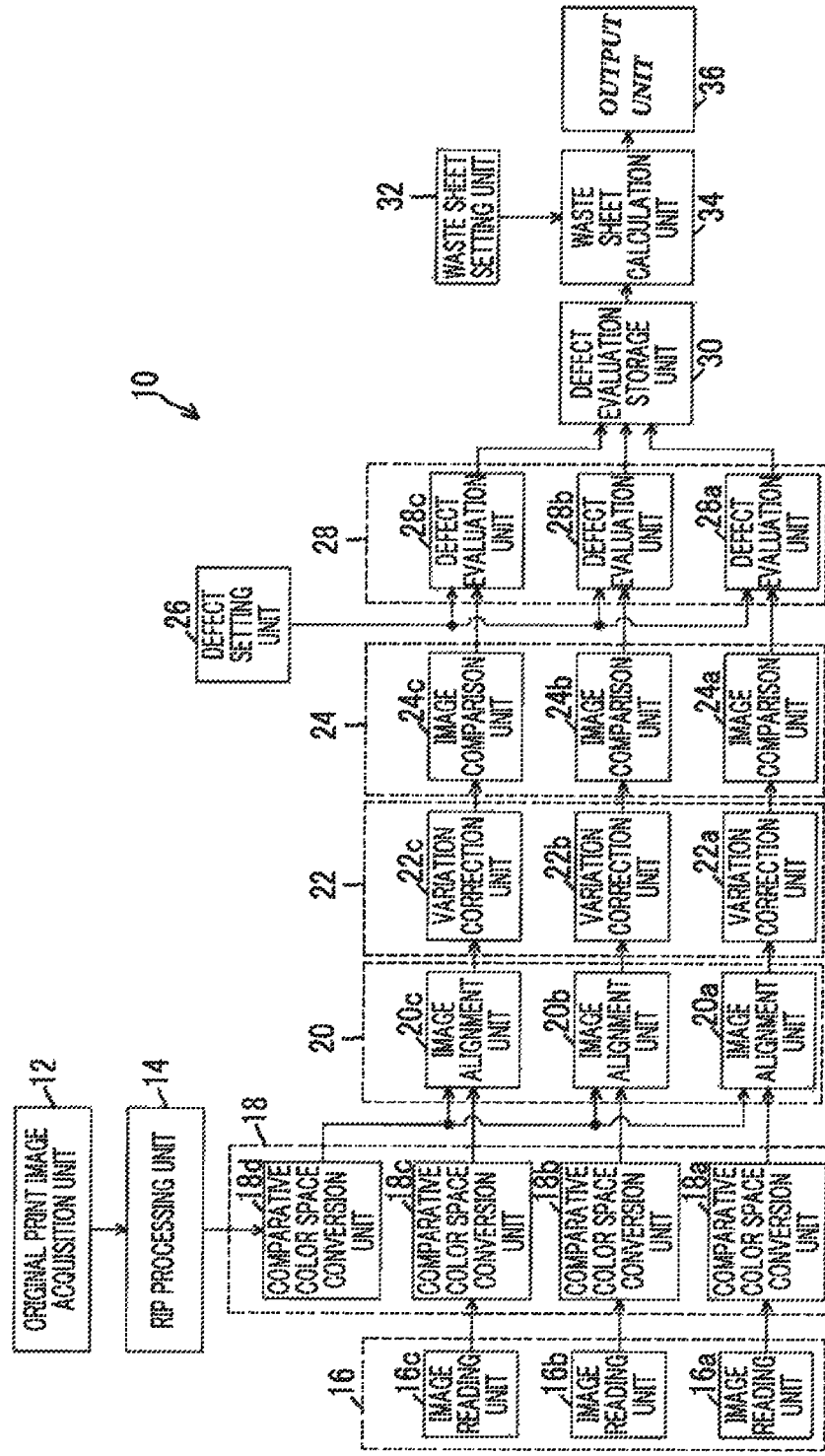

FIG. 2A
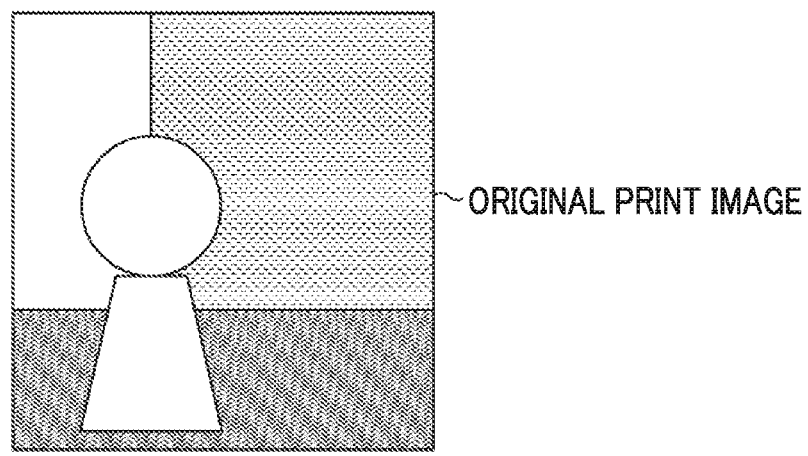
ORIGINAL PRINT IMAGE
FIG. 2B
DIVIDED AND READ IMAGE a   DIVIDED AND READ IMAGE b   DIVIDED AND READ IMAGE c
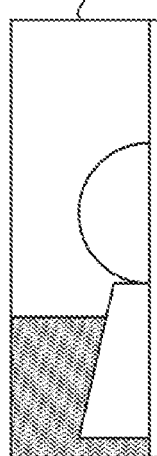 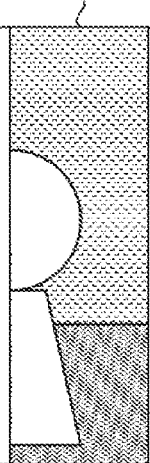 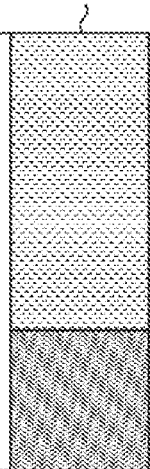

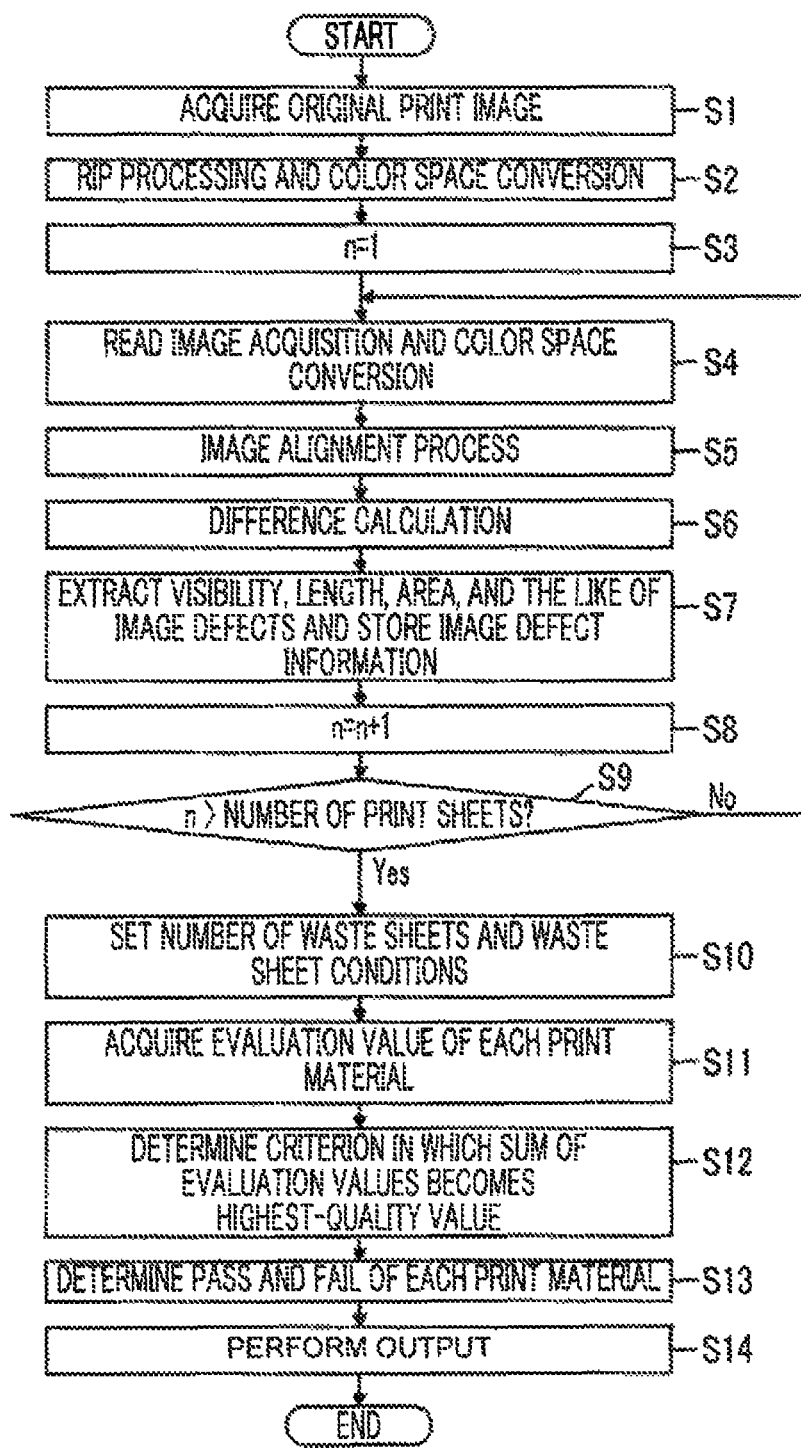

FIG. 4

| TOTAL NUMBER OF PRINT SHEETS | 1000 |
|---|---|
| SET NUMBER OF WASTE SHEETS | 50 |
| DETERMINED WASTE SHEET POSITION | 45-TH<br>100-TH<br>111-TH<br>⋮ |

FIG. 5

| | VISIBILITY<br>A (DISTURBANCE)<br>B (CONCERN)<br>C (NO CONCERN) | LENGTH/AREA | NUMBER |
|---|---|---|---|
| STREAK i | | | |
| CONTAMINATION j | | | |
| UNEVENNESS k | | | |
| CHARACTER LACK l | | | |

DEVICE FOR INSPECTING PRINT MATERIAL, METHOD OF INSPECTING PRINT MATERIAL, AND PROGRAM

CROSS-REFERENCE TO RELATED APPLICATIONS

This application is a Continuation of PCT International Application No. PCT/JP2015/072790 filed on Aug. 11, 2015, which claims priority under 35 U.S.C. § 119(a) to Japanese Patent Application No. 2014-172740 filed on Aug. 27, 2014. Each of the above applications is hereby expressly incorporated by reference, in their entirety, into the present application.

BACKGROUND OF THE INVENTION

1. Field of the Invention

The present invention relates to a device for inspecting a print material, a method of inspecting a print material, and a program, and particularly, to a technology for appropriately controlling the number of failed print materials.

2. Description of the Related Art

Conventionally, in order to print a predetermined output number of print materials, the number of failed print materials is empirically predicted, determined in advance, and included in the number of output sheets, and print is performed. Further, a pass and fail determination as to print materials is performed on the basis of a result of detection of defects such as streaks. A process of detecting this defect is performed according to detection conditions set in advance. Therefore, if detection conditions in a defect detection process are too severe, there is a problem in that the number of failed print materials increases and the number of output sheets cannot be ensured and is insufficient. On the other hand, if the detection condition of the defect detection process is too loose, there is a problem in that surplus print is achieved and productivity is degraded.

JP1994-246904A (JP-H06-246904A) describes a technology for automatically updating reference image data serving as a detection condition according to a change in color tone of a print material which changes as print progresses and determining that the print material is not abnormal with respect to some change in the color tone that is sufficiently allowed in a product. According to this technology, even when the color tone of the print material is different as the print progresses, it is possible to set an appropriate detection condition.

SUMMARY OF THE INVENTION

However, even when the detection conditions are set as in the technology described in JP1994-246904A (JP-H06-246904A), there is a problem in that shortage of the required number of output sheets or surplus print occurs since the number of failed print material is empirically determined.

The present invention has been made in view of such circumstances, and an object of the present invention is to provide a device for inspecting a print material, a method of inspecting a print material, and a program capable of easily achieving both of print cost management and quality control without causing shortage of the number of required output sheets or surplus print by appropriately controlling the number of failed print materials.

An aspect of a device for inspecting a print material in order to achieve the above object comprises: evaluation value acquisition means for inspecting a plurality of print materials and acquiring an evaluation value indicating quality of each print material; allowed-number-of-failed-product acquisition means for acquiring an allowed number of failed products among the plurality of print materials; determination criterion determination means for determining a determination criterion in which the number of failed products is equal to or smaller than the allowed number of failed products and a sum of evaluation values of passed products becomes a highest-quality value; pass and fail determination means for determining pass or fail of each print material on the basis of the determination criterion and the evaluation value of each print material; and output means for outputting a determination result of the pass and fail determination means.

According to the aspect, since a plurality of print materials are inspected, an evaluation value indicating quality of each print material is acquired, an allowed number of failed products among the plurality of print materials is acquired, a determination criterion in which the number of failed products is equal to or smaller than the allowed number of failed products and a sum of evaluation values of passed products becomes a highest-quality value is determined, pass or fail of each print material is determined on the basis of the determination criterion and the evaluation value of each print material, and a determination result of the pass and fail determination means is output, it is possible to appropriately control the number of failed products. Further, since shortage of the required number of output sheets or surplus print is not caused, it is possible to easily achieve both of print cost management and quality control.

Here, the highest-quality value refers to a maximum value in a case where a greater evaluation value is applied when the quality is higher and a minimum value in a case where a smaller evaluation value is applied when the quality is higher.

It is preferable for the evaluation value acquisition means to acquire an evaluation value of each print material on the basis of the visibility of streak of each print material. Thus, it is possible to perform a pass and fail determination on the basis of the visibility of streak of each print material.

It is preferable for the evaluation value acquisition means to acquire an evaluation value of each print material on the basis of the visibility of contamination of each print material. Thus, it is possible to perform a pass and fail determination on the basis of the visibility of contamination of each print material.

It is preferable for the evaluation value acquisition means to acquire an evaluation value of each print material on the basis of the visibility of unevenness of each print material. Thus, it is possible to perform a pass and fail determination on the basis of the visibility of unevenness of each print material.

It is preferable for the evaluation value acquisition means to acquire an evaluation value of each print material on the basis of the visibility of a lack of characters of each print material. Thus, it is possible to perform a pass and fail determination on the basis of the visibility of the lack of characters of each print material.

It is preferable for the evaluation value acquisition means to acquire an evaluation value of each print material on the basis of a viewpoint of at least one of visibility of streak of each print material, visibility of contamination of the print material or visibility of unevenness of the print material, and a viewpoint of visibility of a lack of characters of each print material, and set a weight of the viewpoint of the lack of the characters to be relatively greater than a weight of the viewpoint other than the lack of the characters to acquire the evaluation value of each print material in a case where a plurality of print materials are print materials in which characters are important. Thus, it is possible to perform a pass and fail determination in which character lack is important, on a print material in which characters are important.

It is preferable for the determination criterion determination means to determine, as a determination criterion, an evaluation value at which print materials corresponding to the allowed number of failed products from a low-quality print material among the plurality of print materials arranged in an evaluation order are determined to be failed. Thus, it is possible to determine an appropriate determination criterion.

It is preferable for the output means to be sorting means for sorting and separating passed products and failed products. Thus, it is possible to appropriately output the determination result of the pass and fail determination means.

It is preferable for the output means to be display means for displaying information on at least one of passed products or failed products. Thus, it is possible to appropriately output the determination result of the pass and fail determination means.

An aspect of a method of inspecting a print material in order to achieve the above object comprises: an evaluation value acquisition step of inspecting a plurality of print materials and acquiring an evaluation value indicating quality of each print material; an allowed-number-of-failed-product acquisition step of acquiring an allowed number of failed products among the plurality of print materials; a determination criterion determination step of determining a determination criterion in which the number of failed products is equal to or smaller than the allowed number of failed products and a sum of evaluation values of passed products becomes a highest-quality value; a pass and fail determination step of determining pass or fail of each print material on the basis of the determination criterion and the evaluation value of each print material; and an output step of outputting a determination result in the pass and fail determination step.

According to the aspect, since a plurality of print materials are inspected, an evaluation value indicating quality of each print material is acquired, an allowed number of failed products among the plurality of print materials is acquired, a determination criterion in which the number of failed products is equal to or smaller than the allowed number of failed products and a sum of evaluation values of passed products becomes a highest-quality value is determined, pass or fail of each print material is determined on the basis of the determination criterion and the evaluation value of each print material, and a determination result of the pass and fail determination means is output, it is possible to appropriately control the number of failed products. Further, since shortage of the required number of output sheets or surplus print is not caused, it is possible to easily achieve both of print cost management and quality control.

An aspect of a program that causes a computer to execute a method of inspecting a print material in order to achieve the above object comprises: an evaluation value acquisition step of inspecting a plurality of print materials and acquiring an evaluation value indicating quality of each print material; an allowed-number-of-failed-product acquisition step of acquiring an allowed number of failed products among the plurality of print materials; a determination criterion determination step of determining a determination criterion in which the number of failed products is equal to or smaller than the allowed number of failed products and a sum of evaluation values of passed products becomes a highest-quality value; a pass and fail determination step of determining pass or fail of each print material on the basis of the determination criterion and the evaluation value of each print material; and an output step of outputting a determination result in the pass and fail determination step.

According to the aspect, since a plurality of print materials are inspected, an evaluation value indicating quality of each print material is acquired, an allowed number of failed products among the plurality of print materials is acquired, a determination criterion in which the number of failed products is equal to or smaller than the allowed number of failed products and a sum of evaluation values of passed products becomes a highest-quality value is determined, pass or fail of each print material is determined on the basis of the determination criterion and the evaluation value of each print material, and a determination result of the pass and fail determination means is output, it is possible to appropriately control the number of failed products. Further, since shortage of the required number of output sheets or surplus print is not caused, it is possible to easily achieve both of print cost management and quality control.

According to the present invention, it is possible to easily achieve both of print cost management and quality control.

BRIEF DESCRIPTION OF THE DRAWINGS

FIG. 1 is a block diagram illustrating a schematic configuration of an inspection device.

FIGS. 2A and 2B are diagrams illustrating an example of a print image and divided and read images.

FIG. 3 is a flowchart illustrating a method of inspecting a print material.

FIG. 4 is a diagram illustrating a setting of a print job and waste sheet information in this embodiment.

FIG. 5 is a diagram illustrating image defect information stored in a defect evaluation storage unit.

DESCRIPTION OF THE PREFERRED EMBODIMENTS

Figure 6:
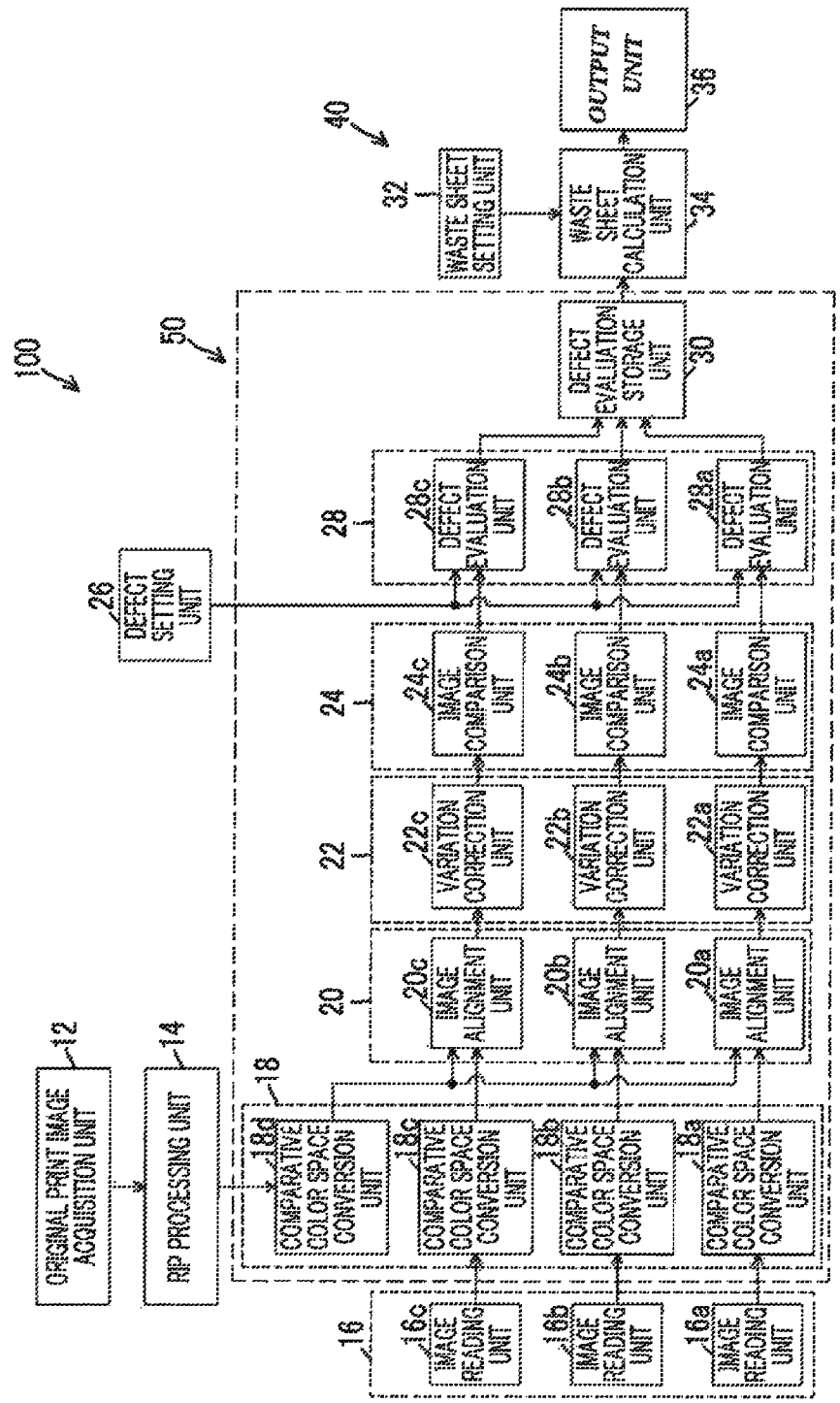
FIG. 6 is a block diagram illustrating a schematic configuration of an inspection system.

Hereinafter, a preferred embodiment of the present invention will be described in detail with reference to the accompanying drawings.

<Entire Configuration of Inspection Device>

A print material inspection device 10 according to this embodiment is a device that inspects a plurality of print materials printed in a print job based on an original print image to acquire an evaluation value indicating quality of each print material, determines a pass and fail determination criterion in which the number of failed products is equal to or smaller than the allowed number of failed products and a sum of evaluation values of passed products becomes a highest-quality value, and determines pass or fail of each print material on the basis of the determined pass and fail determination criterion and the evaluation value of each print material to sort passed print materials (passed products) and failed print material (failed products).

As illustrated in FIG. 1, the inspection device 10 includes an original print image acquisition unit 12, a raster image processor (RIP) processing unit 14, an image reading unit 16, a comparative color space conversion unit 18, an image alignment unit 20, a variation correction unit 22, an image comparison unit 24, a defect setting unit 26, a defect evaluation unit 28, a defect evaluation storage unit 30, a waste sheet setting unit 32, a waste sheet calculation unit 34, and an output unit 36.

The original print image acquisition unit 12 acquires an original print image of a print job that is an inspection target. The original print image is original data of an image printed on a print material in the print job. FIG. 2A illustrates an example of the original print image.

The RIP processing unit 14 performs RIP processing on the acquired original print image. The RIP processing is a conversion process of converting original print image described in a page description language (PDL) or the like into image data in a raster format. For the RIP processing, a known method may be used.

The image reading unit 16 includes a line scanner and divides and reads a print material printed on the basis of the original print image using the line scanner. In this embodiment, one print material is divided in three and read using three image reading units 16*a*, 16*b*, and 16*c*, and three divided and read images are acquired. FIG. 2B illustrates a divided and read image a, a divided and read image b, and a divided and read image c that have been read by the image reading units 16*a*, 16*b*, and 16*c*.

The image reading unit 16 may read the entire print material using one line scanner without dividing and reading the print material or may be input means for acquiring the image read by the line scanner.

The comparative color space conversion unit 18 converts each image into the same color space in order to compare the divided and read image a, the divided and read image b, and the divided and read image c read by the image reading units 16*a*, 16*b*, and 16*c* with the original print image subjected to the RIP processing in the RIP processing unit 14. Here, the comparative color space conversion unit 18*a* performs color space conversion on the divided and read image a, the comparative color space conversion unit 18*b* performs color space conversion on the divided and read image b, the comparative color space conversion unit 18*c* performs color space conversion on the divided and read image c, and the comparative color space conversion unit 18*d* performs color space conversion on the original print image subjected to the RIP processing. For the color space conversion process, a known method can be used.

The image alignment unit 20 performs an alignment process on each divided and read image and the original print image subjected to the color conversion in the comparative color space conversion unit 18 using a correspondence relationship determined by the print conditions as an initial value. Here, the image alignment unit 20*a* performs alignment on the divided and read image a and the original print image, the image alignment unit 20*b* performs alignment on the divided and read image b and the original print image, and the image alignment unit 20*c* performs alignment on the divided and read image c and the original print image. For the alignment process, a known technology such as template matching or a phase-only method may be used.

The variation correction unit 22 removes a variation in a pixel signal at a low frequency caused by the reading of the line scanner from each divided and read image subjected to the alignment process in the image alignment unit 20. Here, a variation correction unit 22*a* removes a variation in an image signal at a low frequency of the divided and read image a, a variation correction unit 22*b* removes a variation in an image signal at a low frequency of the divided and read image b, and a variation correction unit 22*c* removes a variation in an image signal at a low frequency of the divided and read image c.

The image comparison unit 24 compares each divided and read image with the original print image, and calculates a difference of image signals between corresponding pixels. Here, an image comparison unit 24*a* compares the divided and read image a with the original print image, an image comparison unit 24*b* compares the divided and read image b with the original print image, and an image comparison unit 24*c* compares the divided and read image c with the original print image.

The defect setting unit 26 sets a defect evaluation reference value for detecting an image defect from the read divided image. For the defect evaluation reference value, a value according to use or the like of the print material can be set.

The defect evaluation unit 28 detects an image defect of each divided and read image from a difference between the divided and read image and the original print image obtained in the image comparison unit 24 and the defect evaluation reference value set by the defect setting unit 26, and extracts a type, visibility, a length, an area, and the number of detected image defects. Here, a defect evaluation unit 28*a* detects an image defect of the divided and read image a, a defect evaluation unit 28*b* detects an image defect of the divided and read image b, and a defect evaluation unit 28*c* detects an image defect of the divided and read image c.

A type of image defects is classified into streak, contamination, unevenness, and character lack. Here, the streak is a linear image defect caused by landing of dots deviating from an ideal position at the time of printing, and includes a black streak with a higher concentration than the surroundings, and a white streak with a lower concentration than the surroundings. The contamination is an image defect in which an unwanted matter is adhered to a paper, and includes a contamination of paper present prior to printing, and a contamination in which unintended ink is adhered. The unevenness is an image defect that is caused by a concentration distribution serving as a print goal based on the original print image and a concentration distribution resulting from actual print being different. Further, the character lack is an image defect in which a character to be printed cannot be recognized as a character.

The defect evaluation unit 28 includes a streak detection unit, a contamination detection unit, an unevenness detection unit, and a character lack detection unit (not illustrated), which detect image defects including streak, contamination, unevenness, and character lack, respectively.

The defect evaluation storage unit 30 stores a type, visibility, a length, an area, and the number of all image defects extracted by the defect evaluation unit 28.

The waste sheet setting unit 32 (an example of allowed-number-of-failed-product acquisition means) sets number of waste sheets (an example of allowed number of failed product) allowed in a print job that is a target and a waste sheet condition. The waste sheet is a print material to be excluded as a failed print material. The allowed number of waste sheets may be obtained from a difference between the number of all print materials and the number of print materials to be output. Further, as the waste sheet condition, a priority of streak, contamination, unevenness, and character lack is set.

The waste sheet calculation unit 34 (an example of evaluation value acquisition means) calculates the evaluation value of each print material on the basis of the type, visibility, length, area, and the number of all image defects stored in the defect evaluation storage unit 30. Further, the waste sheet calculation unit 34 (one example of determination reference determining means) determines a pass and fail determination criterion in which the number of waste sheets is equal to or smaller than a predetermined number of sheets and a sum of evaluation values of passed print materials becomes a maximum value according to waste sheet conditions. A print material as a waste sheet among all print materials is determined according to the pass and fail determination criterion.

The output unit 36 (an example of pass and fail determination means, output means, and sorting means) sorts passed print materials and waste sheets on the basis of the pass and fail determination criterion determined in the waste sheet calculation unit 34. The output unit 36 can sort the passed print materials and the waste sheets, for example, by transporting all print materials one by one and separating and accumulating the passed print materials and the waste sheets into separate stackers. As another aspect of the output means, display means for displaying information on at least one of the passed print materials or the waste sheets on the basis of the pass and fail determination criterion determined in the waste sheet calculation unit 34 may be provided.

<Method of Inspecting Print Material>

Next, the method of inspecting a print material using the inspection device 10 will be described with reference to FIG. 3. Here, an example in which inspection is performed on all print materials printed on the basis of a print job and passed print materials and waste sheets are sorted will be described. In this print job, a total number of print sheets is set to 1000, and the allowed number of failed print materials (set number of waste sheets) is set to 50, as illustrated in FIG. 4. That is, the number of print materials to be output is 950. The 1000 print materials are assumed to have been already printed.

First, the original print image acquisition unit 12 acquires the original print image (step S1). Subsequently, the RIP processing unit 14 performs RIP processing on the acquired original print image. The original print image after the RIP processing is converted into a color space for image-comparison with the read divided image (for example, L * a * b * space) in the comparative color space conversion unit 18d (step S2).

Then, the variable n is initialized to 1 (step S3). This variable n corresponds to a serial number for distinguishing between print materials.

Then, for the n-th print material among all the print materials, the divided and read images are acquired in the image reading units 16a, 16b, and 16c. The divided and read images are converted into a color space (for example, L * a * b * space) for image-comparison with the original print image in the comparative color space conversion units 18a, 18b, and 18c (step S4).

Subsequently, in the image alignment unit 20, the alignment process is performed on the original print image converted into the color space in step S2 and the divided and read image of the n-th print material converted into the color space in a step S4 (step S5). Further, the variation correction unit 22 removes the variation of the pixel signal at a low frequency caused by reading from the divided and read image after the alignment process. Thereafter, in the image comparison unit 24, a difference in the image signal between corresponding pixels is calculated from the original print image and the divided and read image from which the low frequency variation has been removed (step S6).

Then, in the defect evaluation unit 28, an image defect of each divided and read image is detected from the difference calculated in step S6 and the defect evaluation reference value acquired from the defect setting unit 26. Here, the streak, the contamination, the unevenness, and the character lack are detected as image defects. Further, the defect evaluation unit 28 extracts the type, visibility, length, area, and number of image defects from the detected image defects, and stores these in the defect evaluation storage unit 30 as image defect information of the n-th print material (step S7).

As illustrated in FIG. 5, the visibility, the length/area, and the number are stored for the streak, the contamination, the unevenness, and the character lack. The visibility is classified into three steps including level A of disturbance, level B of concern, and level C of no concern using a position in the image, an average contrast of a background, or shape complexity as parameters.

If the process of extracting the n-th image defect information ends, a variable n increments by 1 (step S8), and it is determined whether or not the variable n is greater than the number (here, 1000) of print sheets, that is, the process of extracting image defect information ends for all print materials (step S9). In a case where the variable n is not greater than the number of print sheets, that is, in a case where there is a print material not subjected to the process of extracting the image defect information, the process returns to step S4 and the same process is repeated for the n-th print material. When the variable n is greater than the number of print sheets, that is, the process of extracting the image defect information ends for all the print materials, the process proceeds to step S10.

In step S10, the waste sheet setting unit 32 sets the number of waste sheets (set number of waste sheets) allowed in the print job that is target and waste sheet conditions (an example of an allowed-number-of-failed product acquisition step; step S10). Here, the allowed number of waste sheets is 50, as described above.

Then, the waste sheet calculation unit 34 calculates an evaluation value indicating the quality of each print material on the basis of the image defect information stored in the defect evaluation storage unit 30 and the waste sheet conditions set by the waste sheet setting unit 32 (an example of an evaluation value acquisition step; step S11). Here, the print grade corresponding to the evaluation value can be determined using Equation 1 below.

$$\text{(print grade)} = \text{(streak weight coefficient)} \times \{\Sigma(\text{streak } i \text{ visibility}) \times \text{length}\} + \text{(contamination weight coefficient)} \times \{\Sigma(\text{contamination } j \text{ visibility}) \times \text{area}\} + \text{(unevenness weight coefficient)} \times \{\Sigma(\text{unevenness } k \text{ visibility}) \times \text{area}\} + \text{(character lack weight coefficient)} \times \{\Sigma(\text{character lack } l \text{ visibility}) \times \text{area}\} \quad \text{(Equation 1)}$$

When the print grade obtained using Equation 1 is zero, the quality is best (highest), and when the value of the print grade increases, the quality is degraded (low). Classification of the visibility illustrated in FIG. 5 is expressed by a value, such as A=3, B=2, and C=1.

Further, a streak weight coefficient, a contamination weight coefficient, an unevenness weight coefficient, and a character lack weight coefficient are waste sheet conditions that are set by the waste sheet setting unit 32, and are parameters having a positive value that are set according to a use or purpose of a print material. For example, in a print material in which characters of a description like drug instructions are important, the character lack weight coefficient is set to a relatively greater value than other coefficients. Thus, it is possible to acquire a print grade in which a weight of a viewpoint of a lack of characters is relatively greater than a weight of a viewpoint other than a lack of characters in a case of a print material in which characters are important.

Subsequently, the waste sheet calculation unit 34 determines a pass and fail determination criterion in which the number of waste sheets is equal to or smaller than the set number of waste sheets (in this case, 50) and a sum of evaluation values of passed print materials (print materials other than the waste sheets among all print materials) becomes a highest-quality value on the basis of the waste sheet conditions set by the waste sheet setting unit 32 (an example of a determination criterion determination step; step S12).

Here, the sum of evaluation values that is the highest-quality value refers to a maximum value in a case where a greater evaluation value is applied when the quality is higher and a minimum value in a case where a smaller evaluation value is applied when the quality is higher. Since the print grade in this embodiment has a smaller value when the quality is higher, the pass and fail determination criterion in which a sum of the print grades of passed print materials becomes a minimum value is determined in this embodiment.

Here, the waste sheet calculation unit 34 arranges all the print materials in a print grade order (an example of an evaluation value order), and determines a print grade in which print materials corresponding to the set number of waste sheets from a print material with a high print grade (that is, a low-quality print material) fail, as the pass and fail determination criterion. That is, when 1000 print materials are arranged in the print grade order (an example of a plurality of print materials in an evaluation value order), the waste sheet calculation unit 34 determines a print grade in which the 50-th print material of the set number of waste sheets from the print material with a high print grade (an example of a low-quality print material) fails and the 51-st print material passes as the pass and fail determination criterion of the evaluation value. In this case, the number of waste sheets becomes equal to or smaller than the set number of waste sheets, and the sum of the print grades of passed print materials becomes a highest-quality value (minimum value). A method of determining the determination criterion in which the number of waste sheets is equal to or smaller than the set number of waste sheets and a sum of evaluation values of passed print materials becomes a highest-quality value is not limited to this example.

Then, the output unit 36 performs a pass and fail determination on each print material on the basis of the pass and fail determination criterion determined in the waste sheet calculation unit 34 (an example of a pass and fail determination step; step S13). That is, the output unit 36 compares the pass and fail determination criterion with the print grade of each print material and sorts a print material with a print grade smaller than the pass and fail determination criterion as a passed print material and a print material with a print grade greater than the pass and fail determination criterion as a failed print material (an example of an output step). FIG. 4 illustrates a case where 45-th, 100-th, 111-th, . . . print materials are waste sheets. Here, 45, 100, and 111 correspond to serial numbers expressed using a variable n.

Finally, the waste sheet sorting unit 36 sorts the passed print materials and the waste sheets on the basis of a result of the pass and fail determination in step S13 (an example of an output step; step S14).

The method of inspecting a print material described above can be configured as a program that causes a computer to execute each step and constitute a non-transitory recording medium (for example, a compact disk-read only memory (CD-ROM)) in which the program is stored.

Further, even when some of the functions of the inspection device 10 are disposed in a server, it is possible to obtain the same effects as in this embodiment.

The system 100 of inspecting a print material illustrated in FIG. 6 includes an inspection device 40 and an inspection server 50. The same units as those of the inspection device 10 illustrated in FIG. 1 are denoted with the same reference numerals, and detailed description thereof will be omitted.

The inspection device 40 includes an original print image acquisition unit 12, an RIP processing unit 14, an image reading unit 16, a defect setting unit 26, a waste sheet setting unit 32, a waste sheet calculation unit 34, and an output unit 36. Further, the inspection server 50 includes a comparative color space conversion unit 18, an image alignment unit 20, a variation correction unit 22, an image comparison unit 24, a defect evaluation unit 28, and a defect evaluation storage unit 30.

The inspection device 40 and the inspection server 50 are connected to each other so that the inspection device 40 and the inspection server 50 can communicate over a network such as a local area network (LAN) or a wide area network (WAN), and can perform the same process as that of the inspection device 10 by performing transmission and reception of information using a predetermined protocol. In the inspection system 100, division of respective functions between the inspection device 40 and the inspection server 50 is not limited to the example illustrated in FIG. 6 and can be appropriately determined.

Further, the inspection device 10 or the inspection system 100 can constitute a printer in combination with various printing means.

A technical scope of the present invention is not limited to the scope described in the embodiments. The configurations or the like in the respective embodiments can be appropriately combined among the respective embodiments without departing from the scope of the present invention.

EXPLANATION OF REFERENCES

10, 40: inspection device
12: original print image acquisition unit
14: RIP processing unit
16: image reading unit
18: comparative color space conversion unit
20: image alignment unit
22: variation correction unit
24: image comparison unit
26: defect setting unit
28: defect evaluation unit
30: defect evaluation storage unit
32: waste sheet setting unit
34: waste sheet calculation unit
36: output unit
50: inspection server
100: inspection system

What is claimed is:

1. A device for inspecting a print material, comprising:
    evaluation value acquisition means for acquiring an evaluation value indicating quality of each print material of a plurality of print materials;
    allowed-number-of-failed-product acquisition means for acquiring an allowed number of failed products among the plurality of print materials;
    determination criterion determination means for determining a determination criterion in which the number of failed products is equal to or smaller than the allowed number of failed products and a sum of evaluation values of passed products becomes a highest-quality value;

pass and fail determination means for determining pass or fail of each print material on the basis of the determination criterion and the evaluation value of each print material; and sorting means for sorting and separating passed products and failed products.

2. The device for inspecting a print material according to claim 1, wherein the evaluation value acquisition means acquires the evaluation value of each print material on the basis of visibility of streak of each print material.

3. The device for inspecting a print material according to claim 1, wherein the evaluation value acquisition means acquires an evaluation value of each print material on the basis of the visibility of contamination of each print material.

4. The device for inspecting a print material according to claim 1, wherein the evaluation value acquisition means acquires an evaluation value of each print material on the basis of the visibility of unevenness of each print material.

5. The device for inspecting a print material according to claim 1, wherein the evaluation value acquisition means acquires an evaluation value of each print material on the basis of the visibility of the lack of characters of each print material.

6. The device for inspecting a print material according to claim 1, wherein the evaluation value acquisition means acquires an evaluation value of each print material on the basis of a viewpoint of at least one of visibility of streak of each print material, visibility of contamination of the print material or visibility of unevenness of the print material, and a viewpoint of visibility of a lack of characters of each print material, and sets a weight of the viewpoint of the lack of the characters to be relatively greater than a weight of the viewpoint other than the lack of the characters to acquire the evaluation value of each print material in a case where a plurality of print materials are print materials in which characters are important.

7. The device for inspecting a print material according to claim 1, wherein the determination criterion determination means determines, as a determination criterion, an evaluation value at which print materials corresponding to the allowed number of failed products from a low-quality print material among the plurality of print materials arranged in an evaluation order are determined to be failed.

8. The device for inspecting a print material according to claim 1, further comprising:

a display for displaying information on at least one of passed products and failed products.

9. The device of claim 1, further comprising:

a computer which executes a program to cause the computer to execute the acquiring of the evaluation value, the acquiring of the allowed number of failed products, the determining of the determination criterion, and the determining of the pass or fail of each print material.

10. A non-transitory computer-readable tangible medium having a program that causes a computer to execute a method of inspecting a print material, the method comprising:

an evaluation value acquisition step of inspecting a plurality of print materials and acquiring an evaluation value indicating quality of each print material;

an allowed-number-of-failed-product acquisition step of acquiring an allowed number of failed products among the plurality of print materials;

a determination criterion determination step of determining a determination criterion in which the number of failed products is equal to or smaller than the allowed number of failed products and a sum of evaluation values of passed products becomes a highest-quality value;

a pass and fail determination step of determining pass or fail of each print material on the basis of the determination criterion and the evaluation value of each print material; and an output step of outputting a determination result in the pass and fail determination step.

11. A device for inspecting print material, comprising:

a computer which executes a program to cause the computer to execute:

setting a number of waste sheets allowed in a print job and a waste sheet condition;

calculating an evaluation value of a print material based on type, visibility, length, area and number of image defects; and determining a pass and fail determination criterion in which the number of waste sheets is equal to or smaller than a predetermined number of sheets and a sum of evaluation values of passed print materials becomes a maximum value according to the waste sheet condition; and a waste sheet sorting unit which sorts passed print materials and waste sheets based on the pass and fail determination criterion.

12. The device of claim 11, wherein the computer executes a program to cause the computer to further execute:

acquiring an original print image;

performing raster image processor (RIP) processing on the acquired original print image;

dividing and reading a print material printed on the basis of the original print image, into a plurality of divided and read images; and converting the plurality of divided and read images into the same color space in order to compare the original print image with each of the plurality of divided and read images.

13. The device of claim 12, wherein the computer executes a program to cause the computer to further execute:

performing an alignment process on the original print image and each of the plurality of divided and read images;

removing a variation in an image signal at a low frequency of each of the plurality of divided and read images;

comparing each of the plurality of divided and read images with the original print image, and calculating a difference of image signals between corresponding pixels;

setting a defect evaluation reference value for detecting an image defect from each of the plurality of divided and read images;

detecting an image defect of each of the plurality of divided and read images based on the defect evaluation reference value; and storing a type, visibility, length, area, and number of the detected image defect, wherein the calculating of the evaluation value comprises calculating the evaluation value based on the stored type, visibility, length, area and number of image defects.

14. The device of claim 13, wherein the original print image comprises original data of an image printed on a print material in a print job.

15. The device of claim 13, wherein the detecting of the image defect comprises detecting an image defect of each of the plurality of divided and read images from the defect evaluation reference value and the calculated difference of image signals.

16. The device of claim 13, wherein the detecting of the image defect comprises extracting a type, visibility, length, area, and number of detected image defects.

17. The device of claim 13, wherein the detecting of the image defect comprises detecting at least one of a streak, a contamination, an unevenness, and a character lack.

18. The device of claim 13, wherein the allowed number of waste sheets is obtained from a difference between the number of all print materials and the number of print materials to be output,
wherein the waste sheet condition comprises a priority of one of streak, contamination, unevenness and character lack, and
wherein the calculating of the evaluation value comprises calculating the evaluation value of each print material on the basis of the type, visibility, length, area, and the stored number of all image defects.

19. A method of inspecting a print material, comprising:
an evaluation value acquisition step of inspecting a plurality of print materials and acquiring an evaluation value indicating quality of each print material;
an allowed-number-of-failed-product acquisition step of acquiring an allowed number of failed products among the plurality of print materials;
a determination criterion determination step of determining a determination criterion in which the number of failed products is equal to or smaller than the allowed number of failed products and a sum of evaluation values of passed products becomes a highest-quality value;
a pass and fail determination step of determining pass or fail of each print material on the basis of the determination criterion and the evaluation value of each print material; and
an output step of outputting a determination result in the pass and fail determination step.

* * * * *